United States Patent
Briffa et al.

(10) Patent No.: US 7,659,715 B2
(45) Date of Patent: Feb. 9, 2010

(54) DEVICE FOR INSPECTING A RECTILINEAR CAVITY WITH EDDY CURRENTS

(75) Inventors: Patrick Briffa, Fontenailles (FR); Patrick Cabanis, Ozouer le Voulgis (FR); Patrick Gaisnon, Cannes Ecluse (FR); Luc Ravize, Bordes (FR)

(73) Assignee: SNECMA, Paris (FR)

( * ) Notice: Subject to any disclaimer, the term of this patent is extended or adjusted under 35 U.S.C. 154(b) by 10 days.

(21) Appl. No.: 12/102,460

(22) Filed: Apr. 14, 2008

(65) Prior Publication Data

US 2008/0265879 A1 Oct. 30, 2008

(30) Foreign Application Priority Data

Apr. 27, 2007 (FR) .................................. 07 54758

(51) Int. Cl.
*G01N 27/82* (2006.01)
(52) U.S. Cl. ..................................... 324/240; 324/228
(58) Field of Classification Search .................. 324/219, 324/228, 232, 234, 237–240, 256–258, 262, 324/220, 241–242
See application file for complete search history.

(56) References Cited

U.S. PATENT DOCUMENTS

| | | |
|---|---|---|
| 5,207,005 A | 5/1993 | Amos et al. |
| 2004/0124834 A1 | 7/2004 | Goldfine et al. |
| 2006/0097719 A1 | 5/2006 | Moore |
| 2006/0109001 A1 * | 5/2006 | Suh et al. ................... 324/232 |

FOREIGN PATENT DOCUMENTS

| | | |
|---|---|---|
| EP | 1 452 863 A1 | 9/2004 |
| EP | 1 659 399 A2 | 5/2006 |

OTHER PUBLICATIONS

U.S. Appl. No. 12/123,029, filed May 19, 2008, Cabanis, et al.
U.S. Appl. No. 12/211,357, filed Sep. 16, 2008, Briffa, et al.
U.S. Appl. No. 12/436,829, filed May 7, 2009, Briffa, et al.

* cited by examiner

*Primary Examiner*—Bot L LeDynh
(74) *Attorney, Agent, or Firm*—Oblon, Spivak, McClelland, Maier & Neustadt, L.L.P.

(57) ABSTRACT

Inspecting an open cavity by successive broaching movements of an eddy-current sensor. The inspection device includes a probe body including the sensor installed laterally in the vicinity of the end of a rod and in line with a ramp, together with a resilient bias device acting on the probe body.

20 Claims, 2 Drawing Sheets

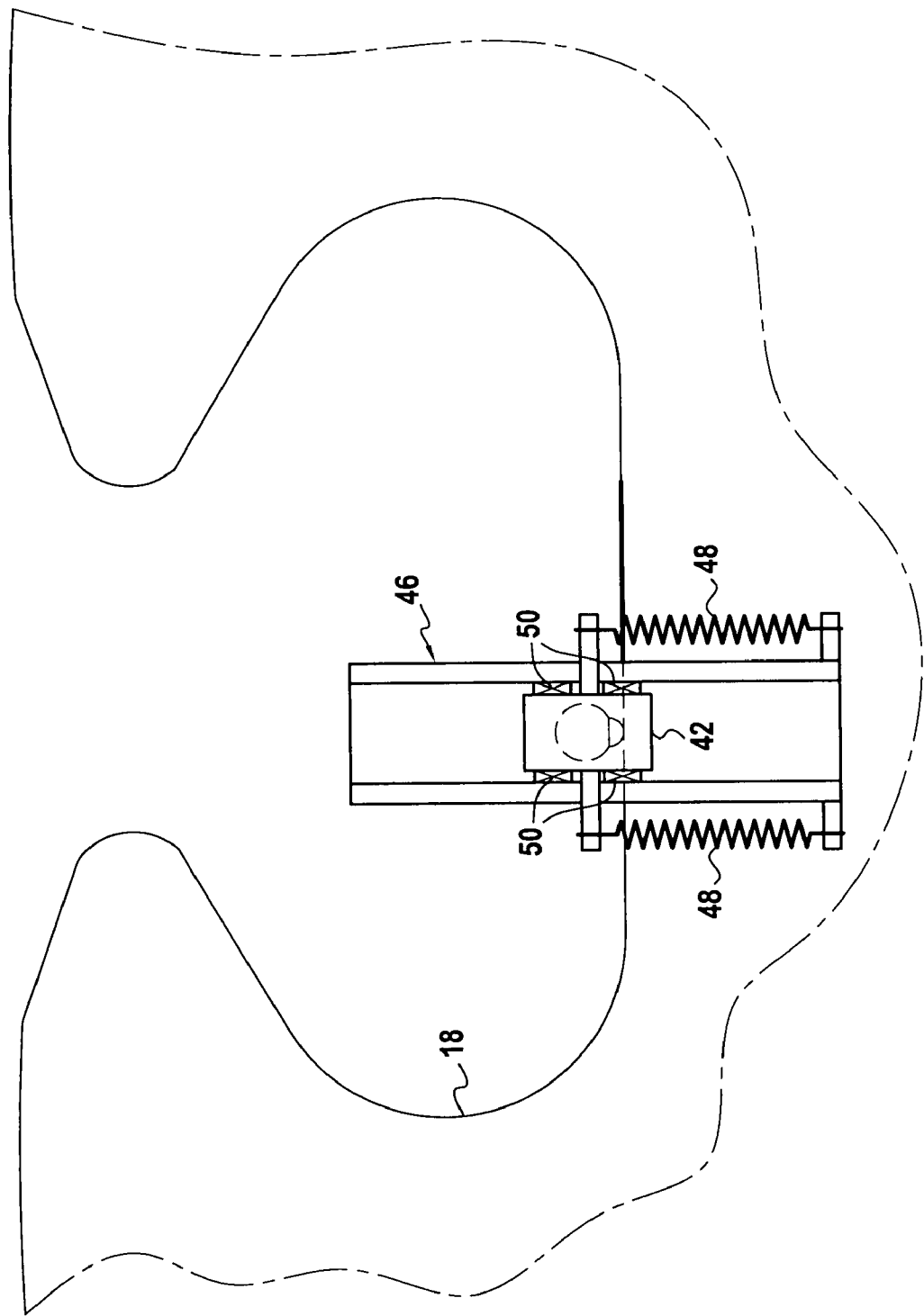

DEVICE FOR INSPECTING A RECTILINEAR CAVITY WITH EDDY CURRENTS

BACKGROUND OF THE INVENTION

The invention relates to a device for non-destructive inspection of an open rectilinear cavity by means of eddy currents, i.e. a cavity that presents an arbitrary section that is substantially constant perpendicularly to a longitudinal direction of the cavity, with inspection being performed by successive broaching movements along the longitudinal direction of said cavity. The invention applies in particular to inspecting tangential slots in a turbojet disk, each slot being for retaining the root of a blade.

With a disk in the new state or in the context of a maintenance operation, the process of inspecting the tangential slots of a turbojet disk is relatively lengthy, difficult, and expensive. Conventionally, eddy-current inspection is used. The complex shape of the slots makes it necessary to develop a probe that is specific to each type of slot. At present, the following difficulties are encountered when developing a high performance system suitable for being automated:
  the probe must be applied to a zone for scanning without any knocks that might damage the sensor;
  the zone for scanning must be swept in a broaching movement that is performed at a speed that is constant over the entire length for inspection, during a broaching stroke;
  edge effects must be reduced; and
  the system must be capable of reliably detecting all kinds of defect, regardless of their orientation relative to the broaching direction.

OBJECTS AND SUMMARY OF THE INVENTION

The invention proposes a novel non-destructive inspection device that uses eddy currents and that enables these objectives to be achieved.

More particularly, the invention provides a device using eddy currents for non-destruction inspection of an open rectilinear cavity, the device comprising:
  a probe body including an eddy-current sensor and a rod, said sensor being installed laterally in the vicinity of a free end of said rod and in line with a ramp extending from said free end; and
  resilient bias means acting on said probe body perpendicularly to said rod to press said probe body against the surface to be inspected, said rod being moved to describe rectilinear strokes along its axis by successive broaching movements, and wherein said sensor is installed substantially at the top of a lateral projection having a curved and regular surface that provides almost point contact for the projection against the surface of said cavity, said ramp being constituted by the portion of the projection that is situated between said free end of the rod and said sensor.

With this arrangement, the sensor is always situated as close as possible to the generator line of the cavity that is being scanned during the broaching stroke. The signal picked up is representative of the surface state of a narrow strip in the vicinity of said generator line. By moving the probe body after each broaching movement, an adjacent parallel zone is explored. Thus, little by little, the entire inside surface of the cavity can be inspected by successive broaching movements.

The specific shape of the probe body, with a ramp in the vicinity of the sensor, makes it possible to make contact with the surface for inspection without knocks during a broaching stroke. In addition, when the sensor comes up to the edge of the orifice of the cavity, its speed has already had time to stabilize while said ramp was in contact with the edge of the cavity.

This curve of shape that is convex and regular avoids vibration (due to almost point contact), that would otherwise lead to disturbances to which eddy currents are particularly sensitive. Measurement reliability is thus improved.

The lateral projection is preferably made of resin, and the sensor (constituted by one or two coils powered with high frequency currents) is embedded in the resin.

Preferably, the sensor is of the differential type. It can thus comprise two adjacent coils, e.g. coils facing each other symmetrically about a plane.

Each coil may be semi-elliptical in section.

To enable all defects to be detected, regardless of their orientation, it is advantageous for said plane to make an angle with the rectilinear travel stroke of the rod, i.e. the broaching direction. For example, said angle may be substantially equal to 45° relative to the broaching direction.

According to another advantageous feature, the above-mentioned resilient bias means include movable equipment carrying the probe body. The movable equipment is mounted to slide along a guide perpendicularly to said rod, and springs are installed between a point of said guide and said movable equipment.

Advantageously, the movable equipment includes ball runners that are movable along said guide.

According to yet another advantageous characteristic, the device includes a robot that is programmed to move said probe body along an outline of an opening of said cavity. The robot enables the position and the orientation of broaching to be varied so as to explore the entire surface for inspection little by little in successive broaching movements. The robot may also be programmed to operate the broaching stroke proper, i.e. to move the probe body along parallel rectilinear strokes.

BRIEF DESCRIPTION OF THE DRAWINGS

The invention can be better understood and other advantages thereof appear more clearly in the light of the following description of an eddy-current inspection device in accordance with the principles of the invention, given purely by way of example and made with reference to the accompanying drawings, in which:

FIG. 5 is a diagrammatic view showing the resilient bias means carrying the probe body.

MORE DETAILED DESCRIPTION

Figure 2:
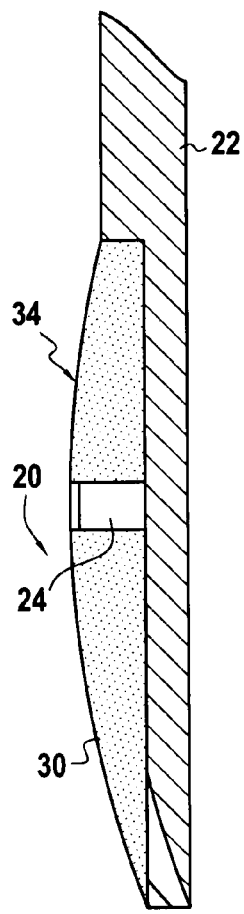
FIGS. 2 and 3 are diagrammatic views showing the probe body.

With reference to the drawings, there can be seen non-destructive inspection device 11 making use of eddy currents, and more specifically in this example for inspecting tangential slots in a disk 14. Each tangential slot is a rectilinear cavity 15 that is open at each end. The section of the cavity perpendicularly to its long direction is substantially constant. The profile of the opening 18 of the cavity is consequently relatively complex and consists in a succession of concave and convex curves presenting different radii of curvature, as can be seen in FIG. 5.

The object is to inspect the inside surface of each cavity by successive broaching movements, i.e. by rectilinear exploration along a longitudinal direction while making contact between a probe and the inside surface of the cavity, along a generator line of the cavity.

For this purpose, the inspection device includes a probe body 20 comprising a rod 22 and an eddy-current sensor 24, together with resilient bias means 26 acting on said probe body 20.

The rod 22 is rigid and the sensor 24 is installed laterally in the vicinity of a free end 28 of the rod. It is situated in line with a ramp 30 that extends away from said end.

The resilient bias means 26 act on the probe body 20 perpendicularly to the rod, so as to press the probe body 20 laterally against the surface to be inspected.

The rod 22 is moved along broaching strokes, so as to describe successive rectilinear movements along its own axis.

Advantageously, the sensor 24 is installed substantially at the tip of a lateral projection 34 of convex surface. The ramp 30 is constituted by the portion of the projection that is situated between the free end 28 of the rod and the sensor 24. Beyond the top of the projection, the convex surface continues until it comes flush with the cylindrical surface of the rod. The lateral projection 34 is preferably made of resin. The sensor 24 is embedded in the resin and comes very nearly flush with the point of greatest thickness (lateral tip) of said projection 34.

The sensor 24 is of the differential type. It can thus be inserted electrically in a Wheatstone bridge to measure variation in impedance.

In this example, the sensor 24 is constituted by two coils 24a and 24b disposed symmetrically about a plane. Each coil is semicircular or semi-elliptical in section, with the rectilinear portions of the coil closely facing opposite sides of a separator 39 that extends in the plane.

Figure 3:
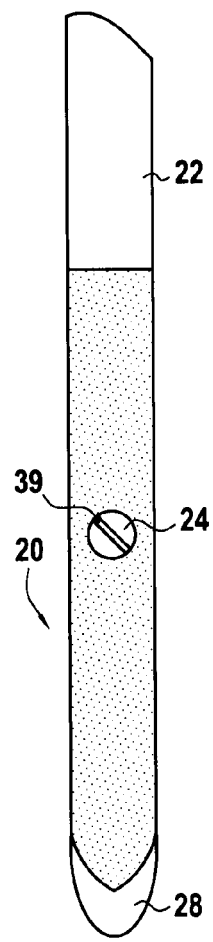
Figure 4:
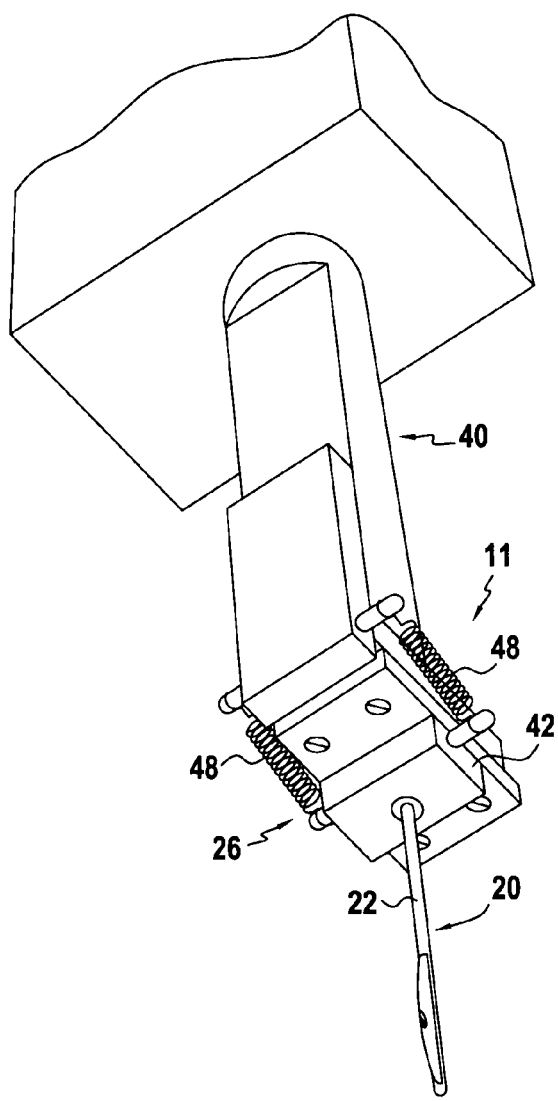
FIG. 4 is a detail view of the sensor.
Figure 4:
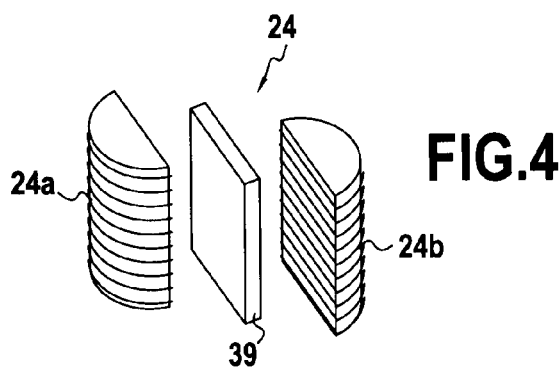
Figure 1:
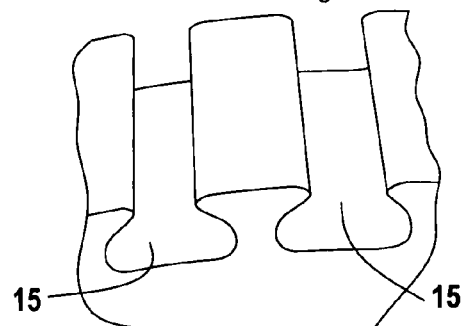
FIG. 1 is a diagrammatic overall perspective view of the installation.

To enable all defects to be detected, including those that are oriented parallel to the broaching axis, the plane of the separator 39 advantageously makes an angle with the rectilinear travel stroke of said rod. In this example, this angle is substantially equal to 45° (see FIG. 3).

The resilient bias means 26 are installed between the end of a robot arm 40 and the body of the probe 20. They comprise movable equipment 42 carrying the probe body, i.e. more particularly the rod 22. Said movable equipment 42 is itself mounted to slide along a guide 46 perpendicular to the rod. Springs 48 are installed between the guide 46 and the movable equipment 42. The movable equipment also includes ball runners 50 that are movable along said guide.

Consequently, the probe body 20 is oriented by the robot in a direction that is selected so that the projection 34 comes into contact with a generator line of the cavity 15, the resilient bias means coming into play to ensure almost point contact between the projection 34 and the inside surface of the cavity, along a generator line that is parallel to the travel direction of the rod.

As mentioned above, the robot that moves both the movable equipment 42 and the rod 22 carrying the sensor is itself programmed to orient and move the probe body 20 to follow the outline of an end opening of the cavity. Each position that is determined by the robot corresponds to a broaching stroke. The broaching movement is imparted in this example by the robot itself, which is suitable for moving the probe along rectilinear strokes parallel to the axis of the rod 22. In a variant, the moving equipment may be fitted with an actuator that performs this broaching movement.

The transverse profile of the cavity is programmed in the form of successive paths (broaching strokes) by appropriately numerically controlling the robot. The part for inspection is positioned on a turntable.

After calibration, the rod 22 is positioned to come into contact with a rectilinear zone for examination. During a broaching stroke, the probe is put into contact with the surface to be inspected, it is moved parallel to the longitudinal direction of the rod, and it scans the surface along a generator line thereof. Given the shape of the projection 34, the sensor can dock within the cavity without jerking and the shape of the ramp 30 makes it possible to avoid acceleration and deceleration stages. This ensures that contact is made progressively between the sensing element (the sensor 24) and the surface, thereby reducing edge effects.

The signal delivered by the sensor is filtered and displayed on a screen. The image is representative of the inspection performed.

The device described above is adaptable to a numerically-controlled rectangular coordinate machine, or to any other automatic or manual tooling fitted with suitable encoders.

What is claimed is:

1. A device using eddy currents for non-destruction inspection of an open rectilinear cavity, the device comprising:
    a probe body including an eddy-current sensor and a rod, said sensor being installed laterally in the vicinity of a free end of said rod and in line with a ramp extending from said free end; and
    resilient bias means for acting on said probe body perpendicularly to said rod to press said probe body against the surface to be inspected, said rod being moved to describe rectilinear strokes along its axis by successive broaching movements, and wherein said sensor is installed substantially at the top of a lateral projection having a curved and regular surface that provides almost point contact for the projection against the surface of said cavity, said ramp being constituted by the portion of the projection that is situated between said free end of the rod and said sensor.

2. A device according to claim 1, wherein said rod is rigid, its movement perpendicularly to the broaching path being imparted by said resilient bias means.

3. A device according to claim 1, wherein said lateral projection is made of resin.

4. A device using eddy currents for non-destruction inspection of an open rectilinear cavity, the device comprising:
    a probe body including an eddy-current sensor and a rod, said sensor being installed laterally in the vicinity of a free end of said rod and in line with a ramp extending from said free end; and
    resilient bias means for acting on said probe body perpendicularly to said rod to press said probe body against the surface to be inspected, said rod being moved to describe rectilinear strokes along its axis by successive broaching movements, and wherein said sensor is installed substantially at the top of a lateral projection having a curved and regular surface that provides almost point contact for the projection against the surface of said cavity, said ramp being constituted by the portion of the projection that is situated between said free end of the rod and said sensor,
    wherein said sensor is of the differential type having two adjacent coils.

5. A device according to claim 4, wherein the two coils are symmetrical about a plane.

6. A device according to claim 5, wherein said plane makes an angle with said rectilinear travel stroke of said rod.

7. A device according to claim 6, wherein said angle is substantially equal to 45°.

8. A device using eddy currents for non-destruction inspection of an open rectilinear cavity, the device comprising:

a probe body including an eddy-current sensor and a rod, said sensor being installed laterally in the vicinity of a free end of said rod and in line with a ramp extending from said free end; and resilient bias means for acting on said probe body perpendicularly to said rod to press said probe body against the surface to be inspected, said rod being moved to describe rectilinear strokes along its axis by successive broaching movements, and wherein said sensor is installed substantially at the top of a lateral projection having a curved and regular surface that provides almost point contact for the projection against the surface of said cavity, said ramp being constituted by the portion of the projection that is situated between said free end of the rod and said sensor, wherein said resilient bias means include movable equipment carrying said probe body, wherein said movable equipment is mounted to slide along a guide perpendicular to said rod, and wherein springs are installed between said guide and said movable equipment.

9. A device according to claim 8, wherein said movable equipment comprises ball runners that are movable along said guide.

10. A device according to claim 1, further comprising a robot programmed to move said probe body along an outline of an opening of said cavity.

11. A device according to claim 10, wherein said robot is also programmed to move said probe body along abovementioned rectilinear strokes.

12. A device according to claim 10, wherein said robot includes a robot arm connected to said rod, and said resilient bias means include at least one spring installed between said robot arm and said rod.

13. A device according to claim 8, wherein said rod is rigid, its movement perpendicularly to the broaching path being imparted by said resilient bias means.

14. A device according to claim 8, wherein said lateral projection is made of resin.

15. A device according to claim 8, wherein said sensor is of the differential type having two adjacent coils.

16. A device according to claim 8, wherein the two coils are symmetrical about a plane.

17. A device according to claim 16, wherein said plane makes an angle with said rectilinear travel stroke of said rod.

18. A device according to claim 17, wherein said angle is substantially equal to 45°.

19. A device according to claim 8, further comprising a robot programmed to move said probe body along an outline of an opening of said cavity.

20. A device according to claim 19, wherein said robot is also programmed to move said probe body along abovementioned rectilinear strokes.

* * * * *